Figure 1:
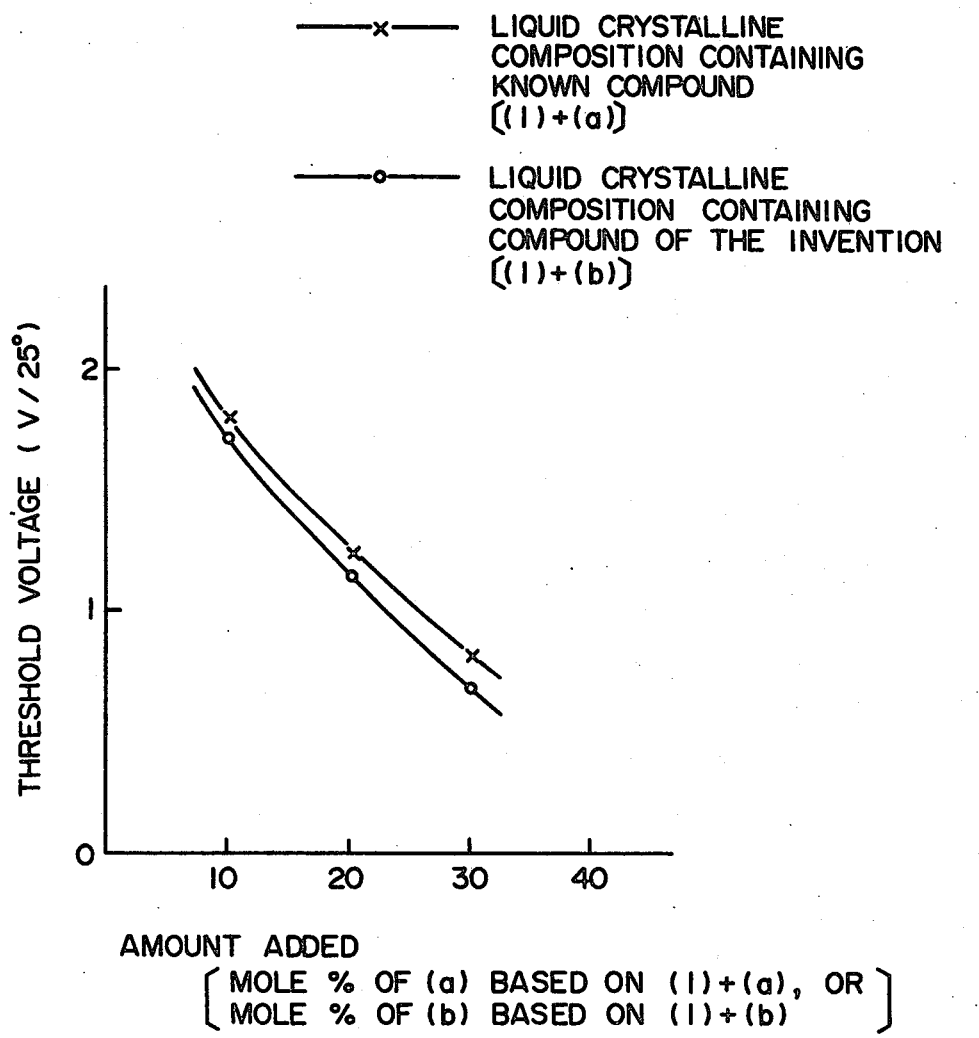

United States Patent [19]

Sasaki et al.

[11] 4,455,261
[45] Jun. 19, 1984

[54] 4-N-ALKYLBENZOYLOXY-3'-FLUORO-4'-CYANOBENZENES

[75] Inventors: Makoto Sasaki, Okegawa; Haruyoshi Takatsu, Kodaira; Hisato Sato, Tokyo; Tuneo Shimamura, Chiba; Kazuhisa Toriyama; Tamihito Nakagomi, both of Mobara, all of Japan

[73] Assignees: Dainippon Ink and Chemicals, Inc.; Hitachi, Ltd., both of Tokyo, Japan

[21] Appl. No.: 439,192

[22] Filed: Nov. 4, 1982

[30] Foreign Application Priority Data

Nov. 11, 1981 [JP] Japan ................................ 56-179618

[51] Int. Cl.³ ...................... C07C 121/75; C09K 3/34
[52] U.S. Cl. .............................. 260/465 D; 252/299.67
[58] Field of Search ............... 260/465 D; 252/299.67

[56] References Cited

U.S. PATENT DOCUMENTS 4,198,312  4/1980  Sato et al. ........................ 252/299

FOREIGN PATENT DOCUMENTS 54-90144  11/1979  Japan .

Primary Examiner—Dolph H. Torrence
Attorney, Agent, or Firm—Sherman & Shalloway

[57] ABSTRACT

A compound represented by the general formula

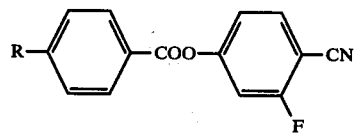

wherein R represents a linear alkyl group having 1 to 10 carbon atoms.

7 Claims, 2 Drawing Figures

4-N-ALKYLBENZOYLOXY-3'-FLUORO-4'-CYANO-BENZENES

This invention relates to a novel nematic liquid crystalline compounds which is an ester derivative useful as an electro-optical display material. The novel nematic liquid crystalline compound provided by this invention is a 4-n-alkylbenzoyloxy-3'-fluoro-4'-cyanobenzene represented by the following general formula

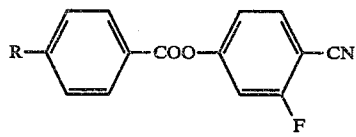

wherein R represents a linear alkyl group having 1 to 10 carbon atoms.

One typical liquid crystalline display cell is the field effect mode cell proposed by M. Schadt, et al. [APPLIED PHYSICS LETTERS, 18, 127–128 (1971)]. The field effect mode cell has two parallel-aligned transparent electrode plates with a nematic liquid crystalline substance having positive dielectric anisotropy filled between the electrode plates. The molecules of the liquid crystalline substance form a helical arrangement at a certain twist angle with their long axes being oriented parallel to the electrode plates, and as a result, have a certain level of rotatory power on the incident light. When a voltage is applied to the electrode plates, the liquid crystal molecules are oriented with their long axes being aligned perpendicular to the electrode plates, whereby their rotatory power disappears. This change in rotatory power is converted to a change in the optical transmission of the cell by utilizing polarizer plates. Hence, the nematic liquid crystalline materials for use in the field effect mode cell should have positive dielectric anisotropy.

The compounds of formula (I) are nematic liquid crystalline compounds. Accordingly, various nematic liquid crystalline substances can be applied to field effect mode cells by including small amounts of the compounds of formula (I). One of the important problems in the art is to operate the field effect mode cells at low voltages. For this purpose, the threshold voltages of nematic liquid crystalline materials used should be lowered as much as possible. The liquid crystalline compounds of formula (I) very effectively serve this purpose. Since the compounds of formula (I) have very strong positive dielectric anisotropy, mixing of these compounds in small amounts with various nematic liquid crystalline materials can result in a striking decrease in their threshold voltage values.

If a compartment having very strong positive dielectric anisotropy but lacking the properties of a nematic liquid crystalline compound is mixed with various nematic liquid crystalline materials, it brings about the disadvantage that the temperature of transition from a nematic phase to an isotropic liquid phase (N-I transition) is drastically decreased, and the range of the service temperature of the mixture is narrowed. Since, however, the compounds of formula (I) show a nematic phase, even the mixing of these compounds in large amounts with various nematic liquid crystalline materials does not cause a drastic decrease in the N-I transition temperature. Accordingly, by using the compounds of formula (I), liquid crystals for low voltage operation can be easily produced without greatly narrowing the nematic temperature range.

The compounds of this invention represented by formula (I) can be produced by a two-stage reaction, as schematically shown below.

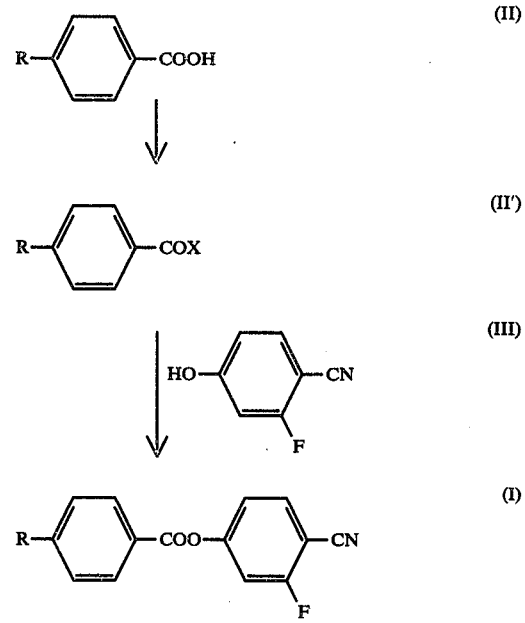

In the first stage, the compound of formula (II) in which R is as defined (the definition of R is the same hereinafter) is reacted with a halogenating agent to produce the compound of formula (II') wherein X represents a halogen atom. In the compound of formula (II'), X is preferably a chlorine atom. Thionyl chloride may be used as the halogenating agent. The reaction is carried out under atmospheric pressure at the refluxing temperature of the reaction mixture. The compound of formula (II') need not to be isolated from the mixture formed as a result of the reaction, and it is only sufficient to remove the excess halogenating agent.

The crude compound of formula (II') produced in the first stage is then reacted in the second stage with the compound of formula (III) in an inert organic solvent, for example diethyl ether, tetrahydrofuran, dimethylformamide or benzene. To remove the hydrogen halide liberated during the reaction out of the reaction system, it is desirable to include a basic substance such as pyridine and tertiary amines in the inert organic solvent. The reaction is carried out under atmospheric pressure at a temperature in the range of from room temperature to the refluxing temperature of the reaction mixture. The reaction product is then subjected to a series of purifying procedures including solvent extraction, water washing, drying, recrystallization, etc. to separate the desired compound of formula (I).

Typical compounds of formula (I) so produced have the transition temperature tabulated below. In the table, C denotes a crystal, N, a nematic phase; and I, an isotropic liquid.

| R in formula (I) | C → I (°C.) | N ⇌ I (°C.) |
|---|---|---|
| $C_2H_5$ | 76.5 | 6 |

| R in formula (I) | C → I (°C.) | N ⇌ I (°C.) |
| --- | --- | --- |
| C3H7 | 70 | 18 |
| C4H9 | 14 | 7 |
| C5H11 | 30 | 20 |
| C6H13 | 35 | 8 |
| C7H15 | 24.5 | 22 |

A compound of the following formula

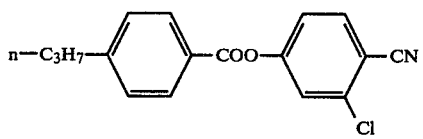
(a)

is known as a typical example of compounds which have a chemical structure similar to the compounds of formula (I) and when added to nematic liquid crystalline materials, make them applicable to field effect mode cells (Japanese Laid-Open Patent Publication No. 90144/1979). The compound of formula (a) has strong positive dielectric anisotropy but lacks the properties of a nematic liquid crystal.

The compound (a) and a typical compound of the invention having the following formula

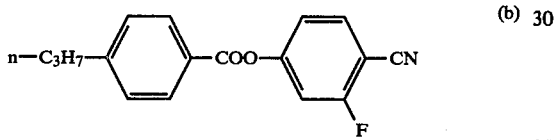
(b)

were each added in various proportions to a typical mixed nematic liquid crystalline material composed of

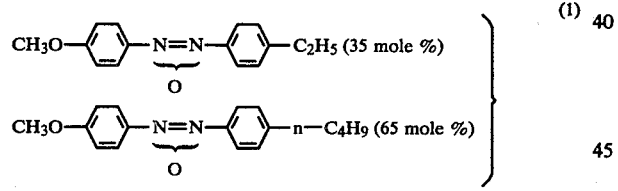
(I)

and the effects of the compounds (a) and (b) on the threshold voltage and the N-I transition temperature of the resulting nematic liquid crystalline materials were tested. The differences shown in FIGS. 1 and 2 of the accompanying drawings were observed.

Figure 2:
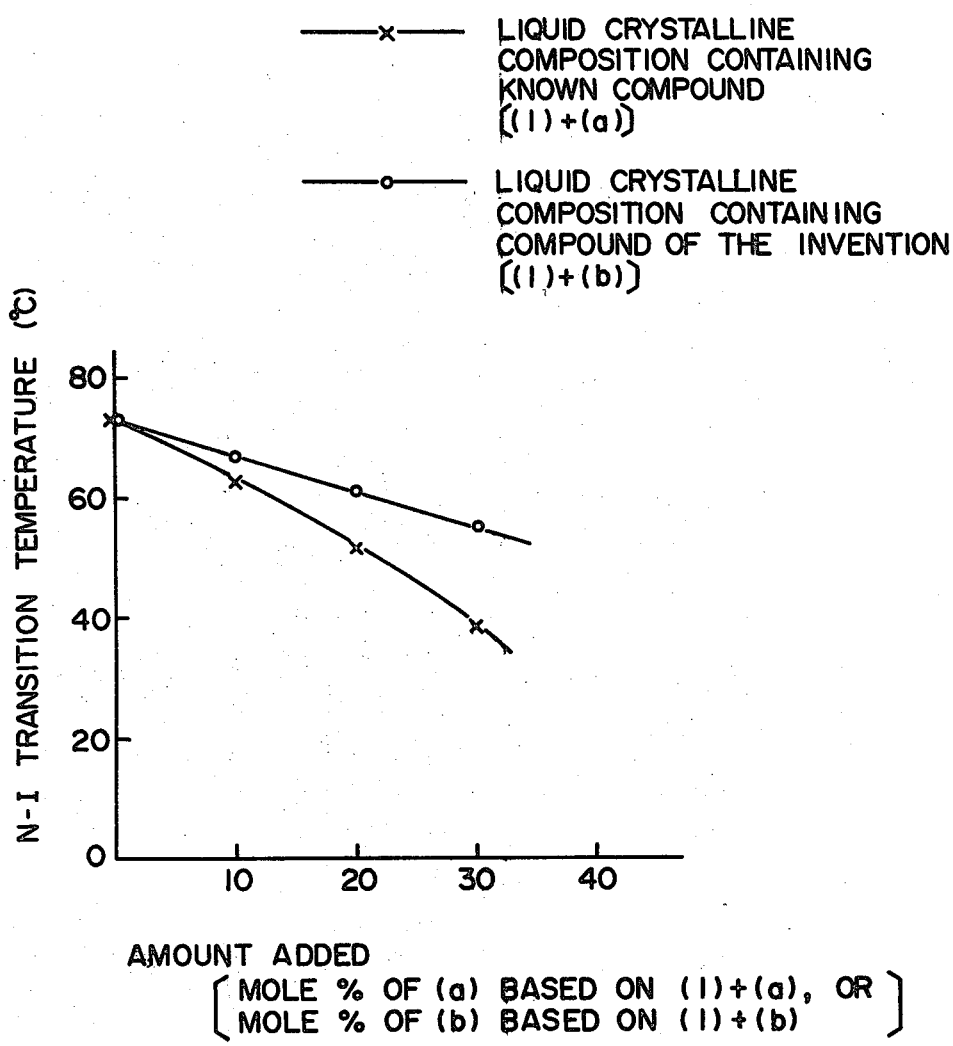

In the accompanying drawings, FIG. 1 is a graph showing the relation between the amount of the compound (a) or (b) added and the threshold voltage of the resulting liquid crystalline material; and FIG. 2 is a graph showing the relation between the amount of the compound (a) or (b) added and the N-I transition temperature of the resulting liquid crystalline material.

The threshold voltage in the above test was determined as follows: The sample was filled in a field effect mode cell in which the liquid crystalline layer had a thickness of 10 microns, and this liquid crystalline cell was used in the measurement of the threshold voltage. A variable voltage of sine waves at 1 KHz was applied to the liquid crystalline cell, and the voltage at which the amount of the transmitted light was 90% was defined as the threshold voltage. The amount (%) of the transmitted light was determined on such a basis that it was taken as 100% when no voltage was applied, and as 0% when the light from a light source was completely shielded.

It will be seen from FIGS. 1 and 2 that where the amount of addition is the same, the compound (b) of the invention can decrease the threshold voltage to a lower level and limit the decrease of the N-I transition temperature to a lesser extent than can the known compound (a).

The following non-limitative examples illustrate the present invention specifically.

EXAMPLE 1

Thionyl chloride (30 cc) was added to 1.69 g (0.010 mole) of a compound of the formula

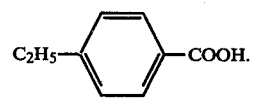

The mixture was reacted under reflux for 30 minutes, and then the excess thionyl chloride was evaporated. To the resulting reaction product were added 1.37 g (0.010 mole) of a compound of the formula

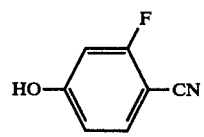

20 cc of benzene and 1.1 g of pyridine, and they were reacted under reflux for 30 minutes. The reaction mixture was washed with 1% hydrochloric acid and water to make it neutral, and then benzene was evaporated from the reaction mixture. The reaction product was recrystallized from methanol to give 2.0 g (0.0075 mole) of a compound of the following formula.

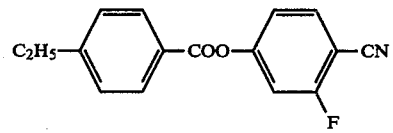

Yield: 75%
Transition temperature: 76.5° C. (C→I), 6° C. (N⇌I)

EXAMPLES 2 TO 6

The following compounds were produced in the same way as in Example 1.

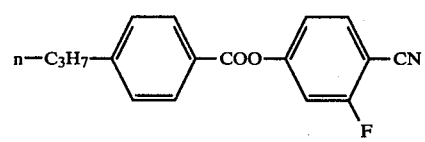
(Example 2)

Yield: 74.5%
Transition temperature: 70° C. (C→I), 18° C. (N⇌I)

(Example 3)

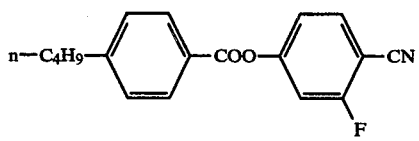

Yield: 73.6%
Transition temperature: 14° C. (C→I), 7° C. (N⇌I)

(Example 4)

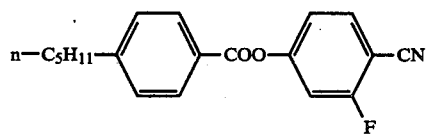

Yield: 75.3%
Transition temperature: 30° C. (C→I), 20° C. (N⇌I)

(Example 5)

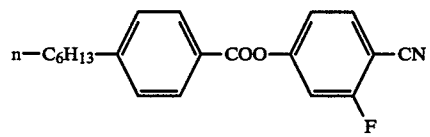

Yield: 76.3%
Transition temperature: 35° C. (C→I), 8° C. (N⇌)

(Example 6)

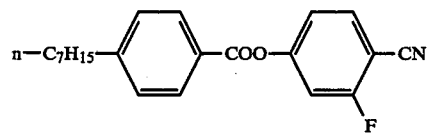

Yield: 75.6%
Transition temperature: 24.5° C. (C→I), 22° C. (N⇌I)

What is claimed is:

1. A compound represented by the general formula

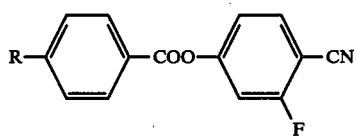

wherein R represents a linear alkyl group having 1 to 10 carbon atoms.

2. A compound of the formula:

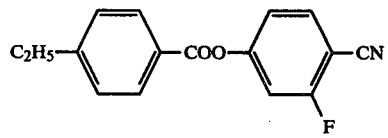

3. A compound of the formula:

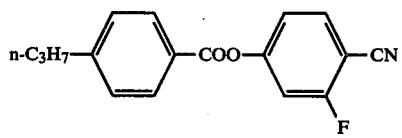

4. A compound of the formula:

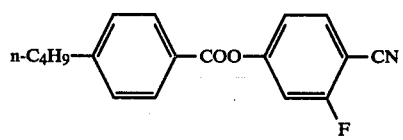

5. A compound of the formula:

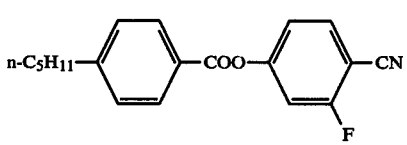

6. A compound of the formula:

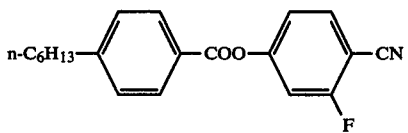

7. A compound of the formula:

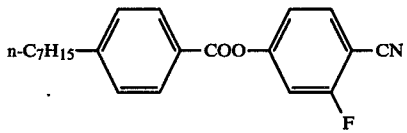

* * * * *